United States Patent [19]
Wolin et al.

[11] Patent Number: 5,985,907
[45] Date of Patent: Nov. 16, 1999

[54] METHOD FOR INHIBITING GROWTH OF METHANOGENS

[75] Inventors: Meyer J. Wolin, Delmar; Terry L. Miller, Slingerlands, both of N.Y.

[73] Assignee: Health Research, Inc., Rensselaer, N.Y.

[21] Appl. No.: 09/133,165

[22] Filed: Aug. 12, 1998

[51] Int. Cl.⁶ .................. A61K 31/40; A61K 31/405; A61K 31/27
[52] U.S. Cl. ............. 514/408; 514/415; 514/481
[58] Field of Search ................. 514/408, 415, 514/481

[56] References Cited

U.S. PATENT DOCUMENTS

| | | | |
|---|---|---|---|
| 3,501,568 | 3/1970 | Haney et al. | 424/115 |
| 3,932,619 | 1/1976 | Brannon et al. | 424/120 |
| 4,212,880 | 7/1980 | Fisher et al. | 424/274 |
| 4,225,593 | 9/1980 | Davies et al. | 424/185 |
| 4,231,938 | 11/1980 | Monaghan et al. | 260/343.5 |
| 4,232,032 | 11/1980 | Boyle et al. | 424/269 |
| 4,268,510 | 5/1981 | Boyle et al. | 424/248.53 |
| 4,279,894 | 7/1981 | Davies et al. | 424/122 |
| 4,289,784 | 9/1981 | Bochis et al. | 424/274 |
| 4,294,925 | 10/1981 | Liu et al. | 435/84 |
| 4,333,923 | 6/1982 | Beck et al. | 424/115 |
| 4,333,952 | 6/1982 | McDonald | 424/330 |
| 4,346,227 | 8/1982 | Terahara et al. | 560/119 |
| 4,414,206 | 11/1983 | Gordon et al. | 424/177 |
| 4,443,471 | 4/1984 | Davies et al. | 424/279 |
| 4,444,784 | 4/1984 | Hoffman et al. | 424/279 |
| 4,474,789 | 10/1984 | Phillips et al. | 424/263 |
| 5,030,447 | 7/1991 | Joshi et al. | 424/80 |
| 5,180,589 | 1/1993 | Joshi et al. | 424/465 |
| 5,354,772 | 10/1994 | Kathawala | 514/414 |

OTHER PUBLICATIONS

D. Roger Illingworth, M.D, Ph.D., "Therapeutic Use of Lovastatin in the Treatment of Hypercholesterolemia," Clinical Therapeutics, vol. 16, No. 1, 2–26, (1994).

*Primary Examiner*—Kevin E. Weddington
*Attorney, Agent, or Firm*—Heslin & Rothenberg, P.C.

[57] ABSTRACT

Methods and compositions for decreasing the production of methane in ruminant animals, thereby increasing feed utilization efficiency, are disclosed. The methods employ HMG-CoA reductase inhibitors to selectively inhibit the growth of methane-producing bacteria without significantly inhibiting the growth of non-methanogens.

19 Claims, No Drawings

METHOD FOR INHIBITING GROWTH OF METHANOGENS

FIELD OF THE INVENTION

The invention relates to a method of inhibiting the growth of methane-producing bacteria by exposing the bacteria to a growth inhibiting amount of an HMG-CoA reductase inhibitor. Specifically, the present invention is concerned with inhibiting the production of methane by methane-producing bacteria in the forestomach of ruminant animals, thereby improving the efficiency of ruminant feed utilization.

BACKGROUND OF THE INVENTION

Methane is a waste product of the microbial fermentation of animal feed in the forestomach (rumen) of ruminants. Cattle, sheep and goats convert the products of microbial fermentation, for example, acetate, propionate and butyrate, to meat, milk, wool and leather. Inhibition of microbial methane gas production in the rumen can increase the efficiency of production of beneficial animal products.

Fermentation is the result of the collective action of many different genera of microbes, and this collective action produces both waste methane and worthwhile products. One genus of bacteria, Methanobrevibacter, appears to produce all of the methane in the ruminant forestomach. Hence, it is desirable to have an inhibitor of growth of Methanobrevibacter, which would eliminate methane formation and the loss to the atmosphere of about 6 to 13 percent of the energy of animal feed. Conservation of the energy in indispensable products formed by the other rumen microbes would yield greater efficiency of use of animal feed.

Methane produced in domestic ruminants makes a significant contribution to atmospheric methane. Inhibition of its production would also provide an important environmental benefit by eliminating a major contributor to atmospheric warming.

Currently, a variety of compounds is used to increase feed utilization efficiency and decrease methane production. Monensin (U.S. Pat. No. 3,501,568) and lasalocid are ionophore antibiotics used to alter rumen fermentation. Phthalides enhance propionate production and inhibit methane production in the rumen (U.S. Pat. No. 4,333,923). U.S. Pat. No. 4,225,593 describes the use of aplasmomycin, boromycin and acylated and hydrogenated derivatives thereof to modify rumen metabolism in domestic ruminant animals by reducing the proportion of methane formed, and increasing the proportion of propionate at the expense of methane and/or acetate. Heterocyclic trichloromethyl derivatives (U.S. Pat. No. 4,268,510) have also been used to reduce the production of methane during rumen metabolism and increase the formation of propionate at the expense of acetate, and hence improve the animals' rate of growth and their efficiency of feed utilization.

Prior to applicants' discovery, no antibiotics or drugs were known to inhibit the growth of methanogens without concomitantly inhibiting non-methanogens. Thus it is an important feature of the HMG-CoA reductase inhibitors employed in the present invention that they inhibit the growth of methanogens while minimally inhibiting the growth of non-methane-generating microbes. Few of the commonly used antibiotics that inhibit growth of bacteria or fungi inhibit methanogens.

HMG-CoA reductase inhibitors are well known in the pharmaceutical art to treat hypercholesterolemia in humans. They have not, however, been employed in ruminants.

The present invention relates to the novel use of hydroxymethylglutaryl-CoA reductase inhibitors to inhibit the growth of methane-producing bacteria, and in particular to decrease methane production in ruminant animals, thereby improving feed utilization efficiency.

SUMMARY OF THE INVENTION

In one aspect, the invention relates to the use of hydroxymethylglutaryl-CoA reductase inhibitors to inhibit the growth of methane-producing bacteria.

In another aspect, the invention relates to the use of HMG-CoA reductase inhibitors to inhibit the growth of methane-producing bacteria in the forestomach of ruminant animals. This may be expressed alternatively as a method for reducing ruminal methane production in ruminant animals. The result of the method is an increased efficiency in feed utilization by the animals.

In another aspect, the invention relates to a feed material which incorporates HMG-CoA reductase inhibitors, or to a feed concentrate which may be mixed with conventional feed materials to deliver the appropriate methanogen growth inhibiting dose to the ruminant animals, or administered directly to the animal in the form of an intra-ruminal pellet, bolus or tablet.

In another aspect, the invention relates to a kit for preparing a ruminant feed. The kit includes an HMG-CoA reductase inhibitor and instructions for its use to prepare a ruminant feed.

DETAILED DESCRIPTION OF THE INVENTION

The term "methanogen-growth inhibiting amount", as used herein, refers to an amount of active compound which is sufficient to inhibit the growth of methane-producing organisms. An amount is considered to be sufficient if there is a statistically significant decrease in the number of methanogenic bacteria in the ruminal fluid as determined by methods that enumerate their concentration or activity. Optimally the number of non-methanogenic bacteria in the same sample will remain relatively unchanged, that is, less than 30% decrease will be observed by the same methods.

The term "ruminant" is used in its conventional sense and includes both mature and immature animals. Examples of ruminants are cattle, sheep, deer, goats, musk ox, buffalo, water buffalo and camels.

Presently identified methane-generating bacteria belong to the group Archaea. The predominant genus of Archaea found in the forestomach of cattle, sheep and goats is Methanobrevibacter, and it appears to be responsible for most methane production in ruminants. The non-methane-generating bacteria that have been identified in ruminant forestomach are members of the group Eubacteria.

Presently preferred compounds used to practice the method of the invention are atorvastatin fluvastatin, lovastatin, mevastatin, pravastatin and simvastatin and salts and metabolites thereof. These compounds are disclosed in U.S. Pat. Nos. 4,346,227; 5,030,447; 5,180,589; 4,231,938; 4,444,784; and 5,354,772; which are incorporated herein by reference.

In practicing the present invention, HMG-CoA reductase inhibitors are orally administered to animals in admixture with feed, feed concentrates or supplements, or in dosage forms such as boluses, capsules, tablets, suspensions, emulsions or solutions containing one or more of the inhibitors. These dosage forms are themselves novel and constitute an embodiment of the invention. Formulation of the compounds in such dosage forms can be accomplished by means and methods well known in the veterinary pharmaceutical art. Each individual dosage unit should contain a quantity of the methanogen growth inhibiting compound which has a direct relation to the proper daily dose for the animal to be treated. The effective rumen-modifying amounts of the present compounds may vary depending on many factors, such as, the size of the animal, the species of the animal, the age of the animal, the particular active compound used, the dosage form employed or the particular sensitivity of the particular animal. The determination of an optimum range of an effective amount, based on variables such as those mentioned above, is within the skill of the ordinary artisan. A typical dose for a large ruminant will be in the range of 10 $\mu$g to 10 mg per day.

The present compounds are most conveniently incorporated in a standard feed composition in an appropriate amount to achieve the desired daily dosage. This amount will vary depending upon the amount of feed composition consumed daily by the animal. The present compounds may also be incorporated in a mineral, protein or energy-type feed additive supplement in an appropriate amount to provide an effective methanogen growth inhibiting daily dosage.

For commercial use, it is convenient to provide a feed additive premix, mineral supplement or concentrate containing one or more of the HMG-CoA reductase inhibitors. The feed additive premix or concentrate comprises one or more of the HMG-CoA reductase inhibitors and a physiologically acceptable carrier such as soybean meal or ground corn or other edible feed grade material, mineral mixtures or innocuous diluent, such as an alcohol, a glycol or molasses.

The animal feeds most generally used in conjunction with this invention are composed of various grains, grain mixtures and roughage feeds such as hay, cotton seed hulls, rice hulls, silage, or other high fiber feedstuffs commonly fed to meat, milk and wool producing animals, especially in cattle or sheep feeds.

Examples of physiologically acceptable carriers for premix or concentrate compositions include soybean meal, corn oil, ground corn, ground corn cobs, barley wheat, mineral mixtures containing, for example vermiculite or diatomaceous earth, corn gluten meal, corn distillers' solubles or soy flour. The active ingredient will be used in amounts to satisfy the criteria set forth above. This premix or concentrate is then mixed with the normal diet for the animal by the grower or feed mixer. The above mentioned grains, grain mixtures, roughage feeds, usual additives, carriers and innocuous diluents constitute physiologically acceptable adjuvants for purposes of this invention.

A series of tests described below demonstrate that HMG-CoA reductase inhibitors specifically inhibit the growth of methane-producing bacteria.

Methanobrevibacter strains, designated Z4, Z8, and Z10, were isolated from the bovine rumen and were grown anaerobically using the serum bottle modification of the Hungate technique. The medium used contained the following: $NaHCO_3$, 7.5 g/L; $K_2HPO_4$ 0.3 g/L; $KH_2PO_4$, 0.3 g/L; $(NH_4)_2SO_4$, 0.3 g/L; $NH_4Cl$, 1 g/L; NaCl, 0.6 g/L; $MgSO_4.7H_2O$, 0.12 g/L; $CaCl_2.2H_2O$, 80 mg/L; $MgSO_4.7H_2O$, 30 mg/L; $MnSO_4.H_2O$, 4.5 mg/L; NaCl, 10 mg; $FeSO_4.7H_2O$, 3 mg/L; $CoSO_4.7H_2O$, 1.8 mg/L; $ZnSO_4.7H_2O$, 1.8 mg/L; $CuSO_4.5H_2O$, 100 $\mu$g/L; $AlK(SO_4)_2.12H_2O$, 180 $\mu$g/L; $Na_2MoO_4.2H_2O$, 100 $\mu$g/L; $H_3BO_3$, 100 $\mu$g/L; $Na_2SeO_4$, 1.9 mg/L; $NiCl_2.6H_2O$, 92 $\mu$g/L; nitrilotriacetic acid, 15 mg/L; thiamine HCl, 2 mg/L; D-pantothenic acid, 2 mg/L; nicotinamide, 2 mg/L; riboflavin, 2 mg/L; pyridoxine HCl, 2 mg/L; biotin, 10 mg/L; cyanocobalamin, 20 $\mu$g/L; p-aminobenzoic acid, 100 $\mu$g/L; folic acid, 50 $\mu$g/L; cysteine $HCl.H_2O$, 0.5 g/L; rumen fluid, 100 mL/L; sodium formate, 5 g/L; sodium acetate, 0.5 g/L; glucose, 10 g/L; and yeast extract, 5 g/L. Resazurin (1 mg/L) was added as an oxidation-reduction potential indicator.

Growth inhibition of methanogenic and non-methanogenic bacteria was measured in the following manner. A 0.29 mM stock solution of compactin, which is sold as mevastatin by Sigma Chemical Co. (St. Louis, Mo.) was prepared in 70% ethanol. Prior to bacterial inoculation, 0.1 mL of the mevastatin solution was added to test tubes containing 5 mL of the above-defined medium (final concentration 5.8 nM). Control tubes received 0.1 mL of 70% ethanol or no additive. All tubes also contained 0.15 mL of a solution of 1.25% each of cysteine and sodium sulfide. Each tube was inoculated with 0.5 mL of a methanogenic species or 0.1 mL of a non-methanogenic species and incubated on a rotator at 37 C. Growth was monitored by measuring the optical density of the cultures at 660 nm.

The data in Table 1 demonstrate inhibition of the methanogenic strain Z10. Growth was inhibited after 3 days incubation with mevastatin. In contrast, no inhibition was seen in the non-mevastatin controls. Tables 2 and 3 show similar results for strains Z4 and Z8. No inhibition occurred in the non-methanogenic species of rumen bacteria in the presence of mevastatin. (Table 4).

TABLE 1

| Growth of Z10 | OD | | |
|---|---|---|---|
| Hrs. | No Add | Ethanol | Drug |
| 0.00 | 0.15 | 0.15 | 0.12 |
| 21.17 | 0.64 | 0.54 | 0.16 |
| 47.42 | 0.90 | 0.76 | 0.17 |
| 70.42 | 1.30 | 0.95 | 0.20 |
| 93.17 | terminate | terminate | 0.22 |
| 110.17 | | | 0.25 |
| 142.17 | | | 0.25 |

TABLE 2

| Growth of Z4 | OD | | |
|---|---|---|---|
| Hrs. | No Add | Ethanol | Drug |
| 0.00 | 0.16 | 0.14 | 0.14 |
| 25.50 | 0.25 | 0.33 | 0.18 |
| 48.50 | 0.64 | 0.57 | 0.22 |
| 71.25 | 0.82 | 0.42 | 0.21 |
| 96.25 | 1.20 | 0.21 | 0.22 |
| 120.25 | terminate | 0.19 | 0.20 |
| 144.25 | | 0.26 | 0.21 |
| 216.75 | | 0.26 | 0.21 |

TABLE 3

| Growth of Z8 | OD | | |
|---|---|---|---|
| Hrs. | No Add | Ethanol | Drug |
| 0.00 | 0.15 | 0.14 | 0.14 |
| 25.50 | 0.12 | 0.12 | 0.12 |
| 48.50 | 0.17 | 0.12 | 0.12 |
| 71.25 | 0.39 | 0.16 | 0.15 |

TABLE 3-continued

| Growth of Z8 | OD | | |
|---|---|---|---|
| Hrs. | No Add | Ethanol | Drug |
| 96.25 | 0.60 | 0.44 | 0.13 |
| 120.25 | 0.53 | 1.05 | 0.13 |
| 144.25 | 0.63 | terminate | 0.14 |
| 216.75 | 0.62 | | 0.13 |

TABLE 4

Non-methanogenic bacteria grown in the presence of mevastatin

| | | Growth ($OD_{660nm}$) | |
|---|---|---|---|
| Organism | Incubation (h) | No drug | Drug |
| *Butyrivibrio fibrisolvens* D1 | 28 | 1.80 | 1.90 |
| *Ruminococcus albus* 7 | 23 | 1.99 | 1.80 |
| *Ruminococcus flavefaciens* C94 | 48 | 1.40 | 1.40 |
| *Bacteroides succinogenes* S85 | 48 | 1.20 | 1.20 |
| *Selenomonas ruminantium* HD4 | 18 | 1.70 | 1.70 |

Mevastatin inhibits all strains of Methanobrevibacter, the organism responsible for methane production in the forestomach of the bovine and other ruminants. Rumen species that do not produce methane are not inhibited by mevastatin. The non-methanogenic species tested are representative of bacteria that digest the major plant polysaccharides of the ruminant diet. They also produce the major products that provide the building blocks and energy the animal requires for growth and maintenance.

Prevention of methane production in the rumen by HMG-CoA inhibitors allows the production of products that are useful for the animal, and energy loss in methane released to the atmosphere is minimized. Several studies indicate that co-culture of methanogens with bacteria that produce propionate or succinate, a precursor of propionate, shift fermentations to the production of acetate. *R. flavefaciens* or *Selenomonas ruminantium* produce the following fermentation when grown with a methane-producing organism:

1. Hexose→2 Acetate+4 $H_2$+2 $CO_2$ (*R. flavefaciens* or *Selenomonas ruminantium*).
2. 4 $H_2$+$CO_2$→$CH_4$+2 $H_2O$ (methane-producing organism).
   Sum:
3. Hexose→2 Acetate+$CH_4$+$CO_2$+2 $H_2O$.

When grown by themselves, the non-methanogenic species produce only small amounts of hydrogen because hydrogen accumulation inhibits the production of hydrogen. Since methanogens use the hydrogen to make methane, they allow continuous production of hydrogen by the non-methanogens because hydrogen does not accumulate.

The fermentations of the non-methanogenic species when hydrogen accumulates are:

4. Hexose+$CO_2$→Succinate+Acetate+Formate (*R. flavefaciens*).
5. 1.5 Hexose→2 Propionate+Acetate+$CO_2$ (*Selenomonas ruminantium*).

Therefore, growth with a methanogen suppresses the production of succinate and propionate and increases the formation of acetate and methane. Succinate formed by *R. flavefaciens* and other bacteria is decarboxylated to propionic acid in the forestomach of ruminants. Therefore, methanogenesis in the forestomach results in depression of propionate production, increased production of acetate, and formation of methane. Eructation then removes methane, a waste product of the fermentation, to the atmosphere.

Propionate is the only rumen fermentation product that is gluconeogenic. The ruminant depends on propionate for anabolism, while butyrate and acetate are utilized primarily for energy and for synthesis of lipids. Diminution of precursors of lipids decreases production of animal fat.

In addition to the above hydrogen-sensitive metabolic pathways, non-methanogenic rumen microbes possess mechanisms for production of hydrogen that are insensitive to inhibition by hydrogen. These mechanisms are primarily related to pyruvate production, which is then converted to acetate, hydrogen and carbon dioxide. Hydrogen does not inhibit this conversion. These pathways produce a considerable amount of hydrogen that methanogens completely use. This raises the question of the fate of hydrogen gas in the forestomach if methanogens are inhibited. It is reasonable to expect that bacteria with mechanisms for activating hydrogen for use in their metabolic pathways would use the available hydrogen. As an illustration, we compare the combined fermentations of *B. fibrisolvens* and *S. ruminantium* plus a methanogen with the fermentation of *B. fibrisolvens* and *S. ruminantium* without a methanogen.

*B. fibrisolvens* produces butyrate, formate, hydrogen, and carbon dioxide from carbohydrates. Since formate is essentially equivalent to hydrogen and carbon dioxide in the ecosystem, the fermentation equation is:

6. Hexose→Butyrate+2 $H_2$+2 $CO_2$.

If this fermentation is coupled to the formation of methane, the equation is:

7. Hexose→Butyrate+0.5 $CH_4$+1.5 $CO_2$

Co-fermentation by butyrate-forming bacteria and methanogens does not influence butyrate formation as it does the formation of succinate and propionate by *R. flavefaciens* and *S. ruminantium* and methanogens. The interaction between equation 7 with the fermentation of *S. ruminantium* with a methanogen (equation 3) gives:

8. 2 Hexose→Butyrate+2 Acetate+1.5 $CH_4$+2.5 $CO_2$+ $H_2O$

When drug inhibition of the growth of forestomach methanogens occurs, *S. ruminantium* could use the hydrogen formed by *B. fibrisolvens* to produce the following fermentation:

9. 2 Hexose→2 Propionate+Butyrate+2 $CO_2$.
   (Note that the same fermentation would result from a combination of *R. flavefaciens* and *B. fibrisolvens* in the forestomach because formate is equivalent to $H_2$+$CO_2$ and succinate is decarboxylated to propionate.)

These equations highlight the energetic benefit to the animal of inhibition of methanogenesis. Table 5 compares the free energies of the products of the methane yielding fermentations of *S. ruminantium* and *B. fibrisolvens* plus a methanogen with the fermentation of *S. ruminantium* plus *B. fibrisolvens*. Inhibition of methanogenesis produces a very large energy benefit. Most of it comes from shifting electrons from methane production into production of propionate by *S. ruminantium*. The energy available to the animal of the non-methanogenic fermentation is 1.65 times the methanogenic fermentation.

TABLE 5

Comparison of energy recoveries from methanogenic and non-methanogenic fermentations by *S. ruminantium* and *B. fibrisolvens*

Free energies of formation per hexose fermented

| Products | Methanogenesis | | | S. ruminatium + B. Fibrisolvens | | |
|---|---|---|---|---|---|---|
| | moles/ hexose | kcal/ mol | kcal/ hexose | Moles/ hexose | kcal/ mol | kcal/ hexose |
| Acetate | 1.00 | 88.29 | 88.29 | 0.00 | 88.29 | 0.00 |
| Butyrate | 0.50 | 84.28 | 42.14 | 0.50 | 84.28 | 42.14 |
| Methane | 0.75 | 12.13 | 9.10 | 0.00 | 12.13 | 0.00 |
| Propionate | 0.00 | 86.30 | 0.00 | 2.0 | 86.30 | 172.60 |
| Sum | | | 139.53 | | | 214.74 |
| Net (-methane) | | | 130.43 | | | 214.74 |

Inhibition of methanogenesis provides a large energy benefit to the animal, although it is unlikely to be as large as the benefit shown by the above example because not all major rumen carbohydrate-fermenting microbes interact with methanogens. *Fibrobacter succinogenes*, a major cellulolytic species and members of the genus Prevotella (formerly named Bacteroides), major polysaccharide-using species, form acetate and succinate and do not produce hydrogen in the absence or presence of methanogens. Their fermentations would not be altered by an inhibition of methanogenesis.

The composition of the invention may take the form of a supplemented feedstuff for direct feeding to animals, in which case it will contain from 5 ppm to 3000 ppm of the compound of the invention in admixture with a conventional ruminant feedstuff; or it may take the form of a concentrated premix for dilution with a conventional ruminant feedstuff to produce a supplemented feedstuff suitable for direct feeding, and such a premix will contain from 0.3% w/w to 50% w/w of the compound of the invention in admixture with either a conventional, nutritionally balanced ruminant feedstuff, an inert solid diluent of no energy value, for example ground limestone, or starch or lactose. The HMG-CoA reductase inhibitor is preferably serially diluted with the diluent or carrier in two or more successive stages, to ensure even mixing.

Premixes suitable for dilution with an animal feedstuff may be manufactured by incorporating 10, 25, 50, 100 or 250 g of the HMG-CoA reductase inhibitor in ground limestone so that the final weight of the premix is 500 g. An animal feedstuff suitable for direct feeding to ruminants may be manufactured by intimately mixing this premix with a typical cattle feedstuff, to obtain a ruminant feedstuff containing 10, 25, 50, 100 or 250 g of the compound of the invention per metric ton, according to the concentration of the active ingredient in the premix used.

Typical cattle feedstuffs that may be employed are:

| | cwt | kg |
|---|---|---|
| Dairy Cake | | |
| Barley meal | 10¼ | 512.5 |
| Maize meal | 1 | 50 |
| Decorticated ground nut cake | 1 | 50 |
| Decorticated cotton seed cake | 1 | 50 |
| Extracted cotton seed cake | 1 | 50 |
| Wheat feed | 3 | 150 |
| Feather meal | ¼ | 12.5 |
| Seaweed meal | ¼ | 12.5 |
| Bone meal | ¼ | 12.5 |
| Chalk | ¼ | 12.5 |
| Molasses | 1½ | 75 |
| Vitamins and trace mineral mix | ½ | 12.5 |
| | 20 | 1000.0 |
| Beef Cube | | |
| Barley meal | 11 | 550 |
| Wheat feed | 5¼ | 262.5 |
| Decorticated ground nut cake | ¼ | 12.5 |
| Extracted ground nut cake | 42 lbs. | 18.75 |
| Bone flour | ¼ | 12.5 |
| Chalk | 42 lbs. | 18.75 |
| Salt | 14 lbs. | 6.25 |
| Molasses | 2 | 12.5 |
| Urea | ¼ | 12.5 |
| Vitamins and trace mineral mix | 14 lbs. | 6.25 |
| | 20 cwt. | 1000.00 |

While the specific embodiment of the invention has been shown and described in detail to illustrate the application of the principles of the invention, it will be understood that the invention may be embodied otherwise without departing from such principles.

We claim:

1. A method of inhibiting the growth of a methane-producing bacterium comprising exposing said bacterium to a growth inhibiting amount of an HMG-CoA reductase inhibitor.

2. A method according to claim 1 wherein said bacterium is of the group Archaea.

3. A method according to claim 1 wherein said bacterium is of the genus Methanobrevibacter.

4. The method of claim 1 wherein the HMG-CoA reductase inhibitor is chosen from the group consisting of atorvastatin, fluvastatin, lovastatin, mevastatin, pravastatin and simvastatin and metabolites thereof.

5. The method of claim 1 wherein the methane-producing bacteria to be inhibited are located in the forestomach of a ruminant.

6. A method of inhibiting the growth of methane-producing bacteria in the forestomach of ruminant animals which comprises administering to a ruminant animal a methanogen growth inhibiting amount of an HMG-CoA reductase inhibitor or a physiologically acceptable salt thereof.

7. The method of claim 6 wherein the HMG-CoA reductase inhibitor is chosen from the group consisting of atorvastatin, fluvastatin, lovastatin, mevastatin, pravastatin and simvastatin.

8. The method of claim 6 wherein said ruminants are cattle.

9. The method of claim 6 wherein said ruminants are sheep or goats.

10. The method of claim 6 wherein the HMG-CoA reductase inhibitor is administered to animals in admixture with a solid foodstuff, in feeding water or, for young animals, dissolved or suspended in whole milk or skim milk, or in the form of a slow-release, intra-ruminal pellet or bolus.

11. A method for reducing ruminal methane production in ruminant animals which comprises administering to the animals a methanogen growth inhibiting amount of an HMG-CoA reductase inhibitor.

12. The method of claim 11 wherein said HMG-CoA reductase inhibitor produces inhibition of growth of a methanogenic bacterial species at a concentration which produces less than 30% inhibition of *Ruminococcus albus*.

13. The method of claim 11 wherein said ruminants are cattle, sheep or goats.

14. The method of claim 11 wherein the HMG-CoA reductase inhibitor is chosen from the group consisting of atorvastatin, fluvastatin, lovastatin, mevastatin, pravastatin, and simvastatin.

15. The method of claim 11 wherein the HMG-CoA reductase inhibitor is administered to animals in admixture with an ordinary solid foodstuff, in feeding water or, for young animals, dissolved or suspended in whole milk or skim milk, or in the form of a slow-release, intra-ruminal pellet or bolus.

16. The method of claim 11 wherein said methanogen growth inhibiting amount of HMG-CoA reductase inhibitor is sufficient to inhibit methanogens but insufficient to inhibit non-methanogenic fermentative bacteria in said ruminant animal.

17. A ruminant feed or feed concentrate comprising:

(a) a standard ruminant feed, and (b) a methanogen growth inhibiting amount of an HMG-CoA reductase inhibitor.

18. The feed of claim 17 wherein said HMG-CoA reductase inhibitor is chosen from the group consisting of atorvastatin, fluvastatin, lovastatin, mevastatin, pravastatin, and simvastatin.

19. A kit for preparing a ruminant feed comprising:

(a) an HMG-CoA reductase inhibitor; and (b) instructions for mixing said HMG-CoA reductase inhibitor with a standard ruminant feed.

* * * * *